United States Patent [19]
Bucalo

[11] 3,938,499
[45] Feb. 17, 1976

[54] IMPLANT AND IMPLANTING METHOD AND TOOL

[76] Inventor: Louis Bucalo, 155 Roberts St., Holbrook, N.Y. 11741

[22] Filed: Feb. 5, 1974

[21] Appl. No.: 439,836

Related U.S. Application Data

[62] Division of Ser. No. 359,429, May 11, 1973, Pat. No. 3,815,578.

[52] U.S. Cl. ............................ 128/1 R; 128/334 C
[51] Int. Cl.² .................... A61B 17/11; A61B 19/00
[58] Field of Search ............ 128/1 R, 334 R, 334 C; 3/1

[56] References Cited
UNITED STATES PATENTS

| | | | |
|---|---|---|---|
| 3,221,746 | 12/1965 | Noble | 128/334 R |
| 3,435,823 | 4/1969 | Edwards | 128/334 C |
| 3,464,065 | 9/1969 | Cromie | 3/1 |
| 3,587,115 | 6/1971 | Shiley | 3/1 |
| 3,687,129 | 8/1972 | Nuwayser | 128/1 R |
| 3,820,528 | 6/1974 | Rogers | 128/1 R |

*Primary Examiner*—Dalton L. Truluck
*Attorney, Agent, or Firm*—Steinberg & Blake

[57] ABSTRACT

A method for introducing a valve into a vas deferens, according to which a continuous portion of the vas is deflected to form a pair of flaps while the vas is advanced onto opposed portions of the implanted valve, and these flaps engage each other and project laterally from the lumen of the vas. The flaps are fastened together so that they will grow together and maintain the free ends of the lumen adjacent an intermediate portion of the implanted valve.

1 Claim, 10 Drawing Figures

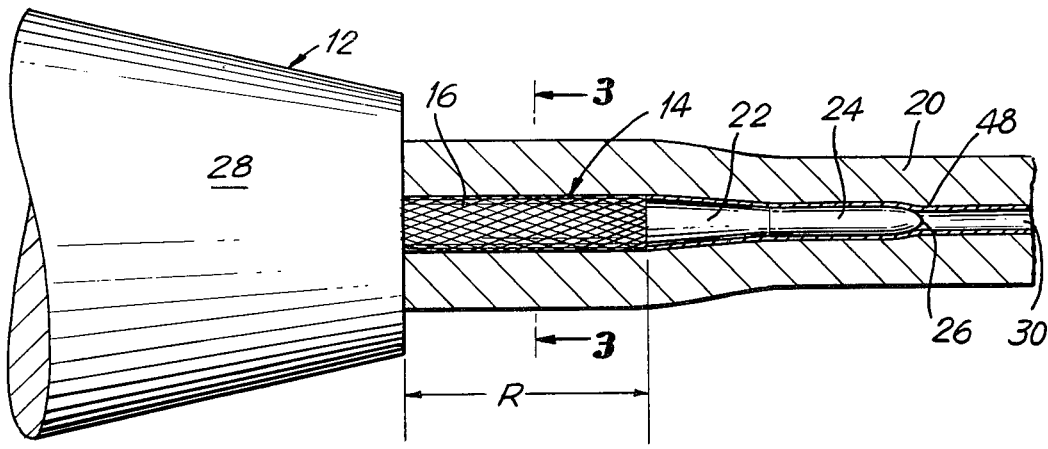
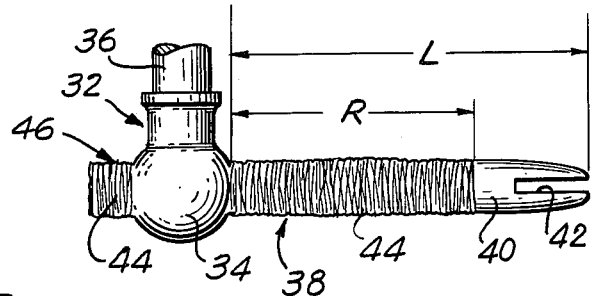
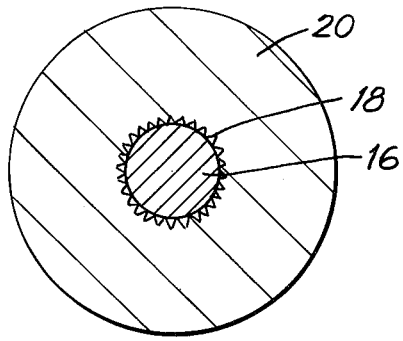
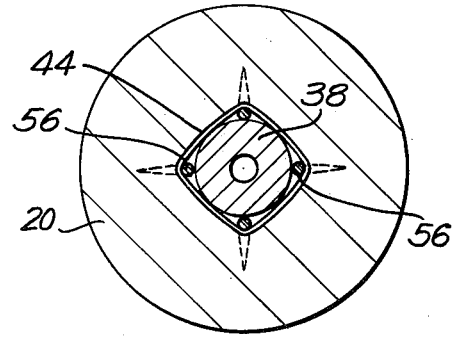
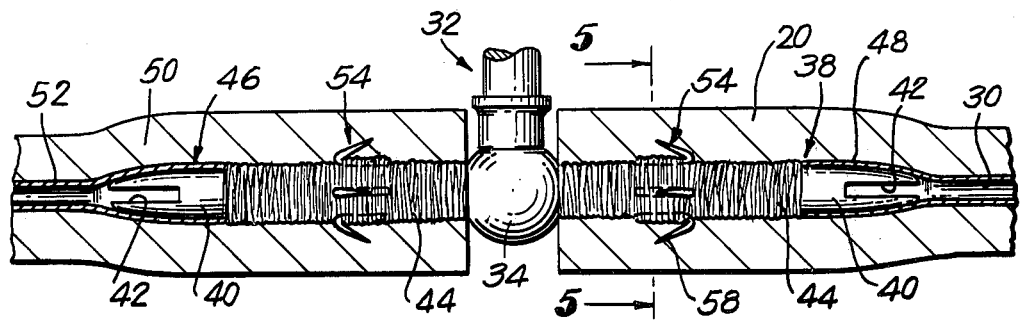

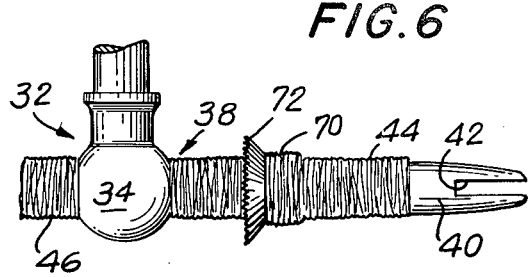
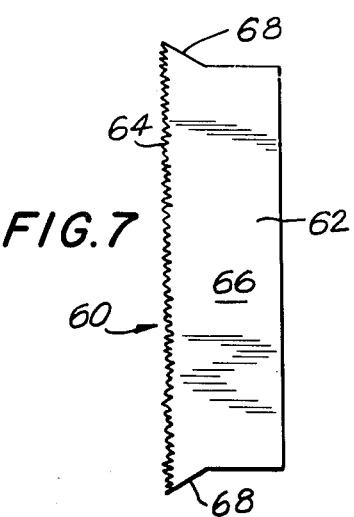
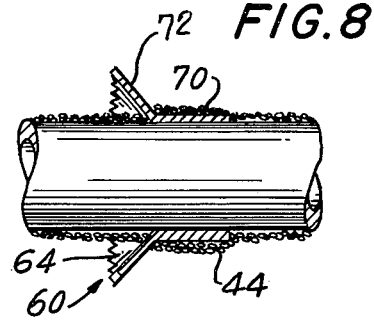
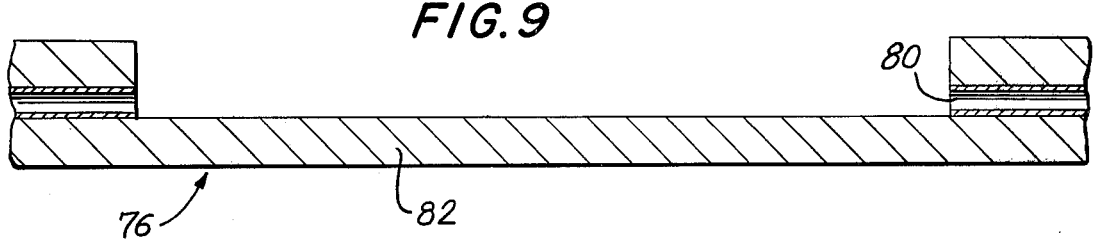
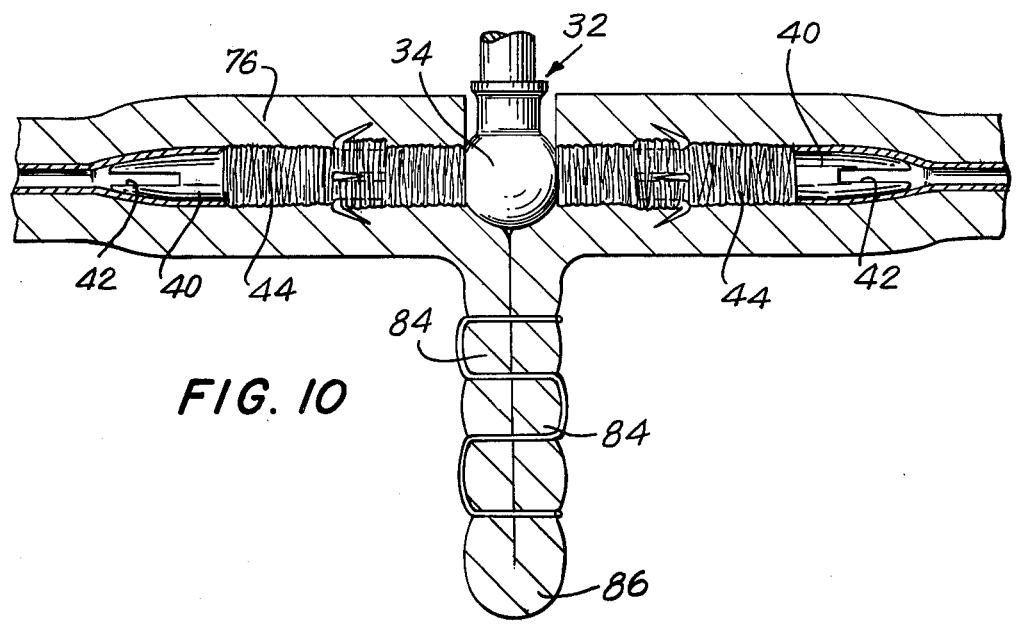

IMPLANT AND IMPLANTING METHOD AND TOOL

CROSS REFERENCE TO RELATED APPLICATION

The present application is a division of application Ser. No. 359,429, filed May 11, 1973, now U.S. Pat. No. 3,815,578 and entitled METHOD OF INSERTING AN IMPLANT INTO A PORTION OF A TUBULAR ORGAN WHOSE MUCOUS LINING HAS BEEN PARTIALLY REMOVED.

BACKGROUND OF THE INVENTION

The present invention relates to implants to be introduced into the bodies of living beings, as well as to tools and methods utilized in connection with the introduction of such implants.

Although it is known to introduce into the body of a living being, such as a human being, artificial implants such as valves for reversibly interrupting the flow of a fluid in a tubular body organ, one of the most serious problems encountered in connection with such implants is that of securely maintaining the implant at the desired location in the body cavity. Because the implant is located in a body of living tissue, particular problems are encountered because while it is essential to secure the implant in the body of living tissue, at the same time it is necessary for nourishment to reach the living tissue, and living tissue has the property of adapting itself to forces which it encounters in such a way that peculiar problems are encountered in the securing of an implant in the interior of a body cavity. Furthermore, problems are encountered in connection with securely mounting an implant of this type in such a way that the flow of a body fluid can be reliably controlled. For example, in the case of a valve, it is essential to secure the valve in the body cavity in such a way that fluid cannot flow along the exterior of the valve, thus defeating the purpose of the valve.

Moreover, the physicians and surgeons who introduce the implant must have a considerable amount of skill in order to securely situate the implant at the desired location in a reliable manner according to conventional techniques. This required skill is relatively rare, so that with many surgeons the implant is situated in a body cavity without the assurance of a reliable securement of the implant.

SUMMARY OF THE INVENTION

It is accordingly a primary object of the present invention to provide a method for implanting which will contribute to elimination of the above drawbacks.

Thus, one of the primary objects of the present invention is to provide an implanting method according to which an exceedingly secure connection of the implant to the body cavity in the interior thereof will be achieved in a simple highly reliable manner which does not require a great amount of skill on the part of the individual who introduces the implant.

Also, it is an object of the present invention to provide an implanting method which will assure a reliable ingrowth of tissue into intimate contact with the exterior surface of the implant, to achieve not only a secure connection of the implant but also to prevent body fluid from flowing along the exterior of the implant.

According to the invention the body cavity is manipulated in such a way that it will not be subject to undesirable slack which could contribute to faulty operation of an implant.

BRIEF DESCRIPTION OF DRAWINGS

The invention is illustrated by way of example in the accompanying drawings which form part of this application and in which:

FIG. 1 is a side elevation of a tool shown schematically in FIG. 1 during use of the tool, with a handle of the tool being fragmentarily illustrated in FIG. 1;

FIG. 2 fragmentarily illustrates an implant, FIG. 2 illustrating the relationship between the tool and the implant;

FIG. 3 is a transverse section of the tool of FIG. 1 taken along line 3—3 of FIG. 1 in the direction of the arrows, the tool being shown by itself in FIG. 3;

FIG. 4 is a schematic longitudinal sectional elevation of a human vas deferens showing an implant of the invention situated in the vas deferens after it has been worked on by the tool of FIG. 1, with the implant of FIG. 4 having a special construction for fixing the vas deferens to the implant;

FIG. 5 is a transverse section of the implant of FIG. 4 taken along line 5—5 of FIG. 4 in the direction of the arrows;

FIG. 6 is a fragmentary elevation of another embodiment of an implant which will accomplish the same results as that of FIGS. 4 and 5;

FIG. 7 is a developed view of a sheet from which the fastening means of FIG. 6 is made;

FIG. 8 is a fragmentary sectional elevation of the fastening means of FIG. 6 and 7 showing in greater detail how it is mounted on the implant;

FIG. 9 is a schematic illustration of how part of a vas deferens is cut away prior to introduction of the implant, in accordance with a feature of the present invention; and FIG. 10 is a schematic representation of how the vas deferens is treated after it has the condition shown in FIG. 9 so as to further contribute to the security of the mounting of the implant in the vas deferens.

DESCRIPTION OF PREFERRED EMBODIMENTS

Referring to FIG. 1, there is illustrated therein a tool 12. This tool 12 is in the form of a reamer having an elongated shank 14 provided with an elongated reaming portion 16. The reaming edges of the elongated shank portion 16 are schematically illustrated in FIG. 1. As is apparent from FIG. 3, the reaming edges 18 of the shank portion 16 project so as to be able to remove material which in the illustrated example is a layer of mucosa which lines the lumen of the vas deferens 20 which is schematically illustrated in FIG. 1.

The tool 12 has at the shank 14 not only the reaming portion 16 but also an elongated tapered portion 22 which has a smooth exterior surface and which gradually tapers so that at its end distant from the reaming portion 16 the portion 22 has a diameter smaller than the portion 16. At this end the portion 22 is followed by a subsequent smooth-surfaced portion 24 of the shank 14 which is of a constant diameter substantially smaller than that of the portion 16, and this portion 24 terminates in a substantially pointed tip 26, shown most clearly in FIG. 1. Thus, after the vas 20 is severed so that an elongated free end portion thereof, as illustrated in FIG. 1, is accessible, the physician or surgeon will introduce into the vas the shank 14 of the tool 12. For convenience in handling, the reaming portion 16 is fixed at its end distant from the portion 22 to a handle 28 which can be grasped for ease of manipulation of the tool. The tip 26 and the portion 24 serves to guide the tool in the interior along the lumen 30 of the vas 20, and when the right end of the handle 28 engages the free end of the vas 20, the reaming portion 16 will be situated as illustrated in FIG. 1 so that by rotation of the reamer, which is manually rotated by manual turning of the handle 28, it is possible to remove from the interior of the vas 20 a layer of mucosa along the portion R of the vas, as illustrated in FIG. 1.

The implant which is to be introduced into the vas is in the illustrated example a valve 32 which is fragmentarily illustrated in FIG. 2 and which is of a previously proposed construction. This valve 32 has the intermediate housing portion 34 in which a valve member is situated to be moved in order to open and close the valve 32. For this purpose the movable part of the valve has a stem 36 which projects beyond the intermediate portion 34 and which can be turned so as to open and close the valve.

At the intermediate portion 34 the valve 32 has a pair of oppositely directed tubular extensions 38 and 46. Extension 38 is shown in FIG. 2 extending to the right from the intermediate portion 34. This tubular extensions 38 serves as the inlet or outlet for the valve when the valve is in its open position. As is illustrated in FIG. 2, the tubular extension 38 terminates in an elongated outer free end portion 40 which is formed with a slot 42 in order to prevent plugging of the open end of the tubular extension 38.

Between the intermediate portion 34 and its smooth-surfaced elongated free end portion 40, the tubular extension 38 carries a means 44 for promoting the ingrowth of tissue. It is to be understood that the tubular extension 46 which is only fragmentarily illustrated in FIG. 2 as extending from the left from the intermediate portion 34 will have a construction identical with the tubular extension 38. Thus, both the extensions 38 and 46 have a means 44 for promoting the ingrowth of tissue. This means 44 in the illustrated example is of a filamentary construction and takes the form of fine wire which is wound around the tubular extension 38 and which is made of a material which is compatible with the human body. This is of course true of all of the materials used for the implant. This fine wire used for the means 44 for promoting the ingrowth of tissue can be gold or platinum, for example. However, the means 44 may also take the form of any suitable porous matrix such as porous metal compatible with the human body and sputtered onto the surface of the extension 38 in an evacuated atmosphere. Any of these constructions are possible for the pair of means 44 respectively carried by the extensions 38 and 46 in order to promote the ingrowth of tissue. It is to be noted that this means 44 extends along the tubular extension 38 through the distance R which is the same distance R along the interior of the vas 20 from which the layer of mucosa is removed by the reamer 12. Thus, the extension 38 has a total length L, and the layer of mucosa is removed only along a distance corresponding to the distance R along the extension 38, so that when the implant is introduced into the vas, the elongated free end portion 40 will extend beyond the region from which the layer of mucosa has been removed by the reamer 12. Thus, the length of the reaming portion 16 is carefully selected to correspond to the distance through which the means 44 extends along the extension 38, and when this extension 38 is introduced into the vas, only that part of the lumen from which the layer of mucosa has been removed will engage the means 44. The remainder of the interior lining of the lumen beyond the means 44 will retain the mucosa layer, so that a layer of mucosa will indeed engage the elongated portion 40.

The extension 46 is treated in precisely the same way as the extension 38. Thus, the other free end of the vas which is not illustrated in FIG. 1 also has a layer of mucosa removed by the tool 12 in precisely the same way so that when the extension 46 is introduced into the other part of the vas only the part of the lumen from which the layer of mucosa has been removed will engage the means for promoting the ingrowth of tissue which is carried by the extension 46. The elongated free end portion thereof which extends beyond the means for promoting ingrowth of tissue will engage the mucosa lining, as described above in connection with the extension 38.

Thus, referring to FIG. 4, it will be seen that the valve 32 is illustrated with its opposed extensions 38 and 46 respectively situated in the lumens of the pair of separated vas portions 20 and 50 which have been separated from each other by cutting through the vas prior to introduction of the implant 32. The vas portion 20 is shown with the mucosa layer 48 extending from the right end of the means 44 carried by the extension 38 for promoting ingrowth of tissue, so that the elongated free end portion 40 is in engagement with the mucosa lining 48. In the same way, the free end portion 40 of the extension 46 engages the mucosa lining 52 of the vas portion 50, this lining 52 extending only up to the means 44 which is carried by the extension 46.

As has been set forth above, one of the important factors in introducing an implant such as the implant 32 into the interior of a body cavity such as the interior of the tubular organ 20 or 50 is the reliable securing of the implant in its position in the interior of the body cavity. Experience has shown that the tissue of the vas portions 20 and 50 will vary rapidly grow into the pair of means 44 for promoting ingrowth of tissue, so that the tissue of the vas portions 20 and 50 will come into intimate tight engagement with the exterior surface of the extensions 38 and 46 at the interstices or pores of the means 44 which promotes the ingrowth of tissue. The removal of the mucosa lining at that part of the organ which engages, at its inner surface, the means 44 contributes in a highly remarkable manner to the rapid ingrowth of tissue in order to achieve the secure connection between the living tissue and the implant.

However, immediately after the implant has been introduced into the lumen of the tubular organ, it is desirable to maintain the tubular organ and the implant connected to each other until the tissue of the organ has an opportunity to grow into the means 44. Thus, it is possible to suture the vas portions 20 and 50 to each other in order to maintain them in the position shown in FIG. 4 until the tissue grows into the means 44 on the extensions 38 and 46. However, such suturing has proved to be a problem since many surgeons cannot perform the suturing in a fully effective manner. Furthermore, such suturing requires an increased time for the operating procedure, which is undesirable.

Therefore, the implant 32 is provided with a fastening means 54 capable of fastening the vas portions 20 and 50 onto the extensions 38 and 46 in a highly reliable manner which will maintain the implant in the position shown in FIG. 4 until the tissue grows into the pair of means 44, without requiring the inconvenient suturing or other measures which may be used to retain the components in the position shown in FIG. 4.

This fastening means 54 in the example of FIGS. 4 and 5 takes the form of a plurality of hooks 56 circumferentially distributed about each of the extensions 38 and 46, in the manner shown most clearly in FIG. 5. Thus in the illustrated example there are four hooks 56 circumferentially distributed about the extensions 38, and four additional hooks 56 are of course circumferentially distributed about the extension 46, in the manner shown in FIG. 5 according to which the hooks are uniformly distributed angularly about each extension. These hooks 56 are also made of a material which is compatible with the human vas such as gold or platinum, for example. The hooks 56 are of a substantially V-shaped configuration and are each provided with one leg extending along the exterior surface of the extension 38 or 46 and held onto the latter by the windings of the wire which forms the means 44, as illustrated in FIGS. 4 and 5. However, any other suitable mounting of the fastening means on the tubular extensions can be used. For example in the case where the means 44 takes the form of a porous matrix, the hooks 56 are initially positioned in engagement with the exterior surface of the tubular extensions and then the deposited matrix will itself serve to fix the hooks 56 to the exterior surface of each of the extensions 38 and 46.

It is to be noted that in addition to a leg which extends along and is fixed to the exterior surface of each extension 38, each hook 56 has an outer inclined leg 58 which terminates in a pointed free end. These inclined legs 58 of the hooks 56 are inclined in such a direction that they permit each extension 38 and 46 to be introduced into the lumen but will prevent removal of each extension. Any attempt at removal will only result in further digging of the hooks 58 into the tissue which forms the vas portions 20 and 50. Thus, these hooks will serve to provide an exceedingly secure connection between the vas portions 20 and 50 and the tubular extensions of the implant 32, so that there will be sufficient opportunity for the tissue to grow into the pair of means 44 to achieve the secure tight connection which will not only securely maintain the implant in the position shown in FIG. 4 but which will also reliably prevent any leakage of fluid along the exterior of the valve.

Of course, the fastening means 54 may have other constructions. For example, as is shown in FIG. 7, it is possible to provide a fastening means 60 formed from a thin sheet of metal 62 which is compatible with the tissue such as gold or platinum. Thus a fairly thin sheet of gold or platinum, for example, may have stamped therefrom sections having approximately the configuration shown in FIG. 7. It will be noted that these sections have a free jagged edge 64 which extends from a substantially rectangular portion 66, with the free edge 64 extending between a pair of oppositely inclined edge regions 68 which project from the substantially rectangular portion 66. The length of the means 60 is such that it can be wrapped at least once around the tubular extensions 38 and 46 in the manner shown in FIG. 6. The wire which is used to form the means 44 can be wrapped around the cylindrical part 70 which is formed from the rectangular portion 66 of the sheet 62. The remaining part, because of the inclined edges 68 and the longer length of the jagged edge 64 forms an outwardly flaring portion 72 terminating in the jagged edge 64 which is thus spaced from the extension 38 and pointed toward the intermediate part 34 of the implant 32, as shown in FIGS. 6 and 8. Thus, the wire which forms the means 44 is securely wrapped around the cylindrical part 70 which is formed from the rectangular portion 62, and part of the wire of the means 44 is also surrounded by the flaring portion 72 which terminates in the jagged edge 64. After the left portion of the wire is wound, as viewed in FIG. 6, the means 60 can be wrapped around the tubular extension 38, and then the remainder of the wire can be wrapped to secure the means 60 in the position shown in FIGS. 6 and 8. In the same way a means 60 is secured to the extension 46.

Therefore, with the embodiment of FIGS. 6–8 when the implant is introduced to the position shown in FIG. 4, the sharp points situated along the jagged edge 64 will dig into the tissue in order to provide an extremely secure mounting while retaining the implant in position within the body cavity in a manner which permits the tissue to grow freely into the means 44 which promotes the ingrowth of tissue.

Thus, both of the embodiments 54 and 60 of a fastening means according to the invention enable the implant to be introduced with substantially no resistance into the interior of the tubular organ but prevents removal of the implant once it has been situated in the organ, enabling the tissue of the latter, particularly the part from which the mucosa layer has been removed, to freely grow into the interstices or pores of the means 44.

According to the invention, a vas deferens 76 which is schematically shown in FIG. 9, has an elongated portion cut away, this portion extending only up to the lumen 80, so that the vas 76 is left with an elongated continuous portion 82 as illustrated in FIG. 9. Then the tool 12 is introduced into the free ends of the lumen which are connected by the portion 82 in order to remove the mucosa layer as described above in connection with FIG. 1.

Thereafter, the implant is introduced, and this implant preferably has a fastening means, such as the fastening means 54 or the fastening means 60.

The elongated portion 82 of the vas is deflected away from the lumen 80 so as to be formed into a pair of flaps 84, as shown in FIG. 10, these flaps of course being integrally connected to each other at their common end 86 which is distant from the vas 76. Then the flaps 84 are simply sutured together.

The result of this feature of the invention is that in addition to all of the advantages discussed above in connection with the other embodiments, the method of FIGS. 9 and 10 will take up any slack which might otherwise undesirably remain in the tubular organ such as the vas deferens. In addition, if it should happen that any sperm should be capable of traveling along the exterior of the valve, this sperm would necessarily be required to transverse the intermediate portion 34 of the implant 32. However, when the sperm reaches one or the other of the flaps 84, the sperm encounters in effect a path extending perpendicularly away from the lumen, and in this way the possibility of any sperm continuing from one to the other side of the implant is avoided to an even greater extent with the arrangement of FIGS. 9 and 10.

It is thus apparent that with the above features of the invention it becomes possible to secure an implant in the exterior of a body cavity in a highly reliable manner, while still making it possible to eliminate any inconveniences in the manipulations which must be performed by a surgeon. The features of the invention are of particular value in connection with the introduction of a valve into a vas deferens for reversibly preventing flow of semen-carrying fluid.

What is claimed is:

1. In a method for introducing a valve having an intermediate portion and tubular extensions respectively extending in opposite directions from said intermediate portion into a vas deferens of a living being, the step of removing a part of the vas deferens extending outwardly from the lumen thereof at only one side of the lumen so as to leave at the vas deferens a continuous portion extending between free ends of the lumen which are exposed by removing said part thereof, introducing the tubular extensions into the free ends of the lumen, respectively, deflecting the continuous portion of the vas deferens away from the lumen thereof to advance the free ends of the lumen toward the intermediate portion of the valve for pulling the vas deferens onto the opposite tubular extensions, forming from the deflected continuous portion of the vas deferens a pair of flaps which engage each other, which remain connected to each other at their outer ends which are distant from the lumen, and which project laterally from the lumen, and fastening the flaps together so that they will grow together and maintain the free ends of the lumen adjacent the intermediate portion of the valve.

* * * * *